US00PP26935P2

(12) United States Plant Patent
van Haaster

(10) Patent No.: US PP26,935 P2
(45) Date of Patent: Jul. 12, 2016

(54) *DAHLIA* PLANT NAMED 'FIDAHGEORGIA'

(50) Latin Name: *Dahlia variabilis*
Varietal Denomination: Fidahgeorgia

(71) Applicant: Johanna G. H. van Haaster, Hillegom (NL)

(72) Inventor: Johanna G. H. van Haaster, Hillegom (NL)

(73) Assignee: Fides B.V., De Lier (NL)

( * ) Notice: Subject to any disclaimer, the term of this patent is extended or adjusted under 35 U.S.C. 154(b) by 154 days.

(21) Appl. No.: 14/120,748

(22) Filed: Jun. 21, 2014

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Keith Robinson
(74) *Attorney, Agent, or Firm* — C. A. Whealy

(57) ABSTRACT

A new and distinct cultivar of *Dahlia* plant named 'Fidahgeorgia', characterized by its relatively compact, upright, somewhat outwardly spreading and mounding plant habit; early and freely flowering habit; large inflorescences with light pink and yellow bi-colored ray florets; and good post-production longevity.

2 Drawing Sheets

Botanical designation: *Dahlia variabilis.*
Cultivar denomination: 'FIDAHGEORGIA'.

BACKGROUND OF THE INVENTION

The present invention relates to a new and distinct cultivar of *Dahlia* plant, botanically known as *Dahlia variabilis* and hereinafter referred to by the name 'Fidahgeorgia'.

The new *Dahlia* plant is a product of a planned breeding program conducted by the Inventor in Hillegom, The Netherlands. The objective of the breeding program is to create new container *Dahlia* plants that have a freely branching and flowering habit, attractive ray floret coloration and good post-production longevity.

The new *Dahlia* plant originated from an open-pollination in Hillegom, The Netherlands of an unnamed selection of *Dahlia variabilis*, not patented, as the female, or seed, parent with an unknown selection of *Dahlia variabilis* as the male, or pollen, parent. The new *Dahlia* plant was discovered and selected by the Inventor as a single flowering plant from within the progeny of the stated open-pollination in a controlled environment in Hillegom, The Netherlands.

Asexual reproduction of the new *Dahlia* plant by cuttings in a controlled environment in Hillegom, The Netherlands since 2009 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fidahgeorgia'. These characteristics in combination distinguish 'Fidahgeorgia' as a new and distinct *Dahlia* plant:

1. Relatively compact, upright, somewhat outwardly spreading and mounding plant habit.
2. Early and freely flowering habit.
3. Large inflorescences with light pink and yellow bi-colored ray florets.
4. Good postproduction longevity.

Compared to plants of the female parent selection, plants of the new *Dahlia* differ primarily in ray floret coloration and plant shape.

Plants of the new *Dahlia* can be compared to plants of *Dahlia* 'Fidahnewy', disclosed in U.S. Plant Pat. No. 21,257. In side-by-side comparisons conducted in De Lier, The Netherlands, plants of the new *Dahlia* differed primarily from plants of 'Fidahnewy' in the following characteristics:

1. Plants of the new *Dahlia* were more vigorous and taller than plants of 'Fidahnewy'.
2. Plants of the new *Dahlia* had daisy-type inflorescences whereas plants of 'Fidahnewy' had decorative-type inflorescences.
3. Plants of the new *Dahlia* and 'Fidahnewy' differed in ray floret color as plants of 'Fidahnewy' had light red purple-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'Fidahgeorgia' grown in a container.

The photograph on the second sheet is a close-up view of a typical inflorescence of 'Fidahgeorgia'.

DETAILED BOTANICAL DESCRIPTION

The aforementioned photographs and the following observations and measurements describe plants grown during the winter in 13-cm containers in a glass-covered greenhouse in De Lier, The Netherlands and under environmental conditions and cultural practices which approximate those generally used in commercial potted *Dahlia* production. During the production of the plants, day temperatures averaged 19° C. and night temperatures averaged 18° C. Plants were nine weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'Fidahgeorgia'.

Parentage:

*Female, or seed, parent*.—Unnamed selection of *Dahlia variabilis*, not patented.

*Male, or pollen, parent*.—Unknown selection of *Dahlia variabilis*, not patented.

Propagation:

*Type*.—By cuttings.

*Time to initiate roots, summer*.—About six days at temperatures of about 22° C.

*Time to initiate roots, winter*.—About eight days at temperatures of about 20° C.

*Time to produce a rooted young plant, summer*.—About twelve days at temperatures of about 22° C.

*Time to produce a rooted young plant, winter*.—About 16 days at temperatures of about 20° C.

*Root description*.—Fine, fibrous; tuber development has not been observed on plants of the new *Dahlia*.

*Rooting habit*.—Freely branching; dense.

Plant description:

*Plant and growth habit*.—Relatively compact, upright, somewhat outwardly spreading and mounding plant form; broad inverted triangle; freely basal branching with about six primary lateral branches developing per plant, each primary lateral branch with numerous secondary branches; inflorescences held above the foliar plane on strong peduncles; bushy and dense habit; moderately vigorous growth habit.

*Plant height*.—About 25 cm.

*Plant diameter or spread*.—About 30 cm.

*Lateral branches*.—Length: About 20 cm. Diameter: About 4 mm. Internode length: About 2 cm to 3.5 cm. Aspect: Erect to somewhat outwardly spreading. Strength: Moderately strong. Texture: Smooth, glabrous. Color: Close to 146B.

Leaf description:

*Arrangement*.—Opposite; leaves may be single or compound with three or occasionally five leaflets.

*Length*.—About 11 cm to 13 cm.

*Width*.—About 6 cm to 7 cm.

*Shape*.—Elongated ovate.

*Apex*.—Acute.

*Base*.—Attenuate.

*Margin*.—Serrate to dentate.

*Venation pattern*.—Pinnate.

*Texture, upper and lower surfaces*.—Slightly pubescent; slightly rough.

*Color*.—Developing leaves, upper surface: Close to N137A. Developing leaves, lower surface: Close to 148B. Fully expanded leaves, upper surface: Close to N147A; venation, close to 138A. Fully expanded leaves, lower surface: Close to 147B; venation, close to 138B.

*Petioles*.—Length: About 3.5 cm to 4.5 cm. Diameter: About 4 mm. Texture, upper and lower surfaces: Smooth, glabrous. Color, upper and lower surfaces: Close to 144C.

Inflorescence description:

*Appearance and arrangement*.—Single-type inflorescence form with ray florets forming acropetally on a receptacle; inflorescences positioned above the foliar plane on strong peduncles; inflorescences face mostly upright; freely flowering habit with about 20 to 40 inflorescences developing per plant.

*Fragrance*.—None detected.

*Time to flower*.—Plants flower continuously from spring through the autumn in The Netherlands; early flowering habit, plants begin flowering about 7 to 7.5 weeks after planting.

*Post-production longevity*.—Inflorescences maintain good substance for about two weeks on the plant; inflorescences persistent.

*Inflorescence buds*.—Height: About 1.2 cm. Diameter: About 1.4 cm. Shape: Globular, flattened. Color: Close to 144C.

*Inflorescence size*.—Diameter: About 10 cm. Depth (height): About 6 cm to 8 cm. Disc diameter: About 1 cm. Receptacle height: About 3 mm. Receptacle diameter: About 1.5 cm to 2 cm.

*Ray florets*.—Quantity per inflorescence: About 40 to 45 arranged in about four to five whorls. Length: About 2.5 cm. Width: About 1.4 cm. Shape: Oblanceolate. Apex: Obtuse to slightly emarginate. Base: Cuneate to obtuse. Margin: Entire. Aspect: Initially upright to roughly perpendicular to the peduncle; ray florets cupped and eventually reflexing. Texture, upper and lower surfaces: Smooth, glabrous. Color: When opening, upper surface: Towards the apex, close to N74B to N74C; mid-section, close to 155B; towards the base, close to 5A. When opening, lower surface: Mid-section and towards the apex, close to 73B fading to close to 155B; towards the base, close to 4A. Fully opened, upper surface: Towards the apex, close to 73A to 73C; mid-section, close to 155B; towards the base, close to 3A; with development, color towards the base becoming closer to 2A. Fully opened, lower surface: Mid-section and towards the apex, close to N74A and 73A; towards the base, close to 2B.

*Disc florets*.—Quantity per inflorescence: About 30 to 40. Length: About 9 mm. Diameter: About 1.5 mm. Shape: Tubular, elongated; apices obtuse. Color, when opening: Apex: Close to 1B. Mid-section: Close to 1C. Base: Close to 1D. Color, fully opened: Apex: Close to 1B. Mid-section and base: Close to 1C.

*Phyllaries*.—Quantity per inflorescence: About eight arranged in a single whorl. Length: About 1 cm to 1.1 cm. Width: About 5 mm. Shape: Ovate. Apex: Acute. Base: Cuneate. Margin: Entire. Texture, upper and lower surfaces: Smooth, glabrous. Color, upper surface: Close to N137A. Color, lower surface: Close to N137B.

*Peduncles*.—Length: About 8 cm to 13 cm. Diameter: About 2.5 mm. Aspect: Mostly erect. Strength: Strong. Texture: Smooth, glabrous. Color: Close to 144B.

*Reproductive organs*.—Androecium: Present on disc florets only. Quantity per floret: About five. Filament length: About 3 mm. Filament color: Close to 17B.

Anther shape: Narrowly elliptic. Anther length: About 8 mm. Anther width: About 1.5 mm. Anther color: Close to 6A. Pollen amount: Abundant. Pollen color: Close to 17B. Gynoecium: Present on ray and disc florets. Quantity per floret: One. Pistil length: About 3 mm. Style length: About 3 mm. Style color: Close to 2A. Stigma color: Close to 7A. Ovary color: Close to 145C. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

Temperature tolerance: Plants of the new *Dahlia* tolerate high temperatures about 35° C. and short periods of low temperatures about 5° to 10° C.

It is claimed:

1. A new and distinct *Dahlia* plant named 'Fidahgeorgia' as illustrated and described.

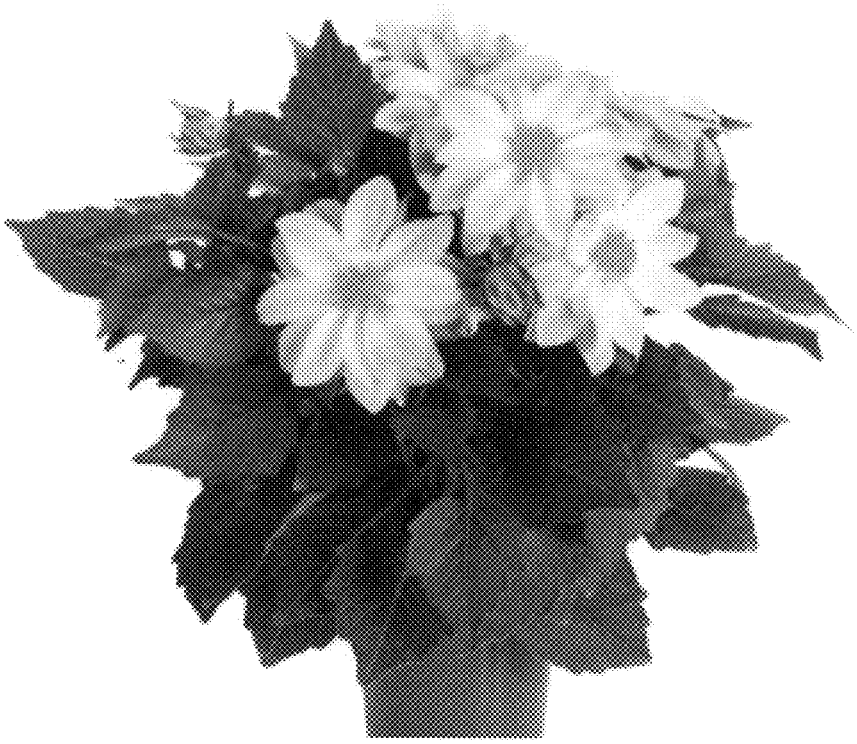

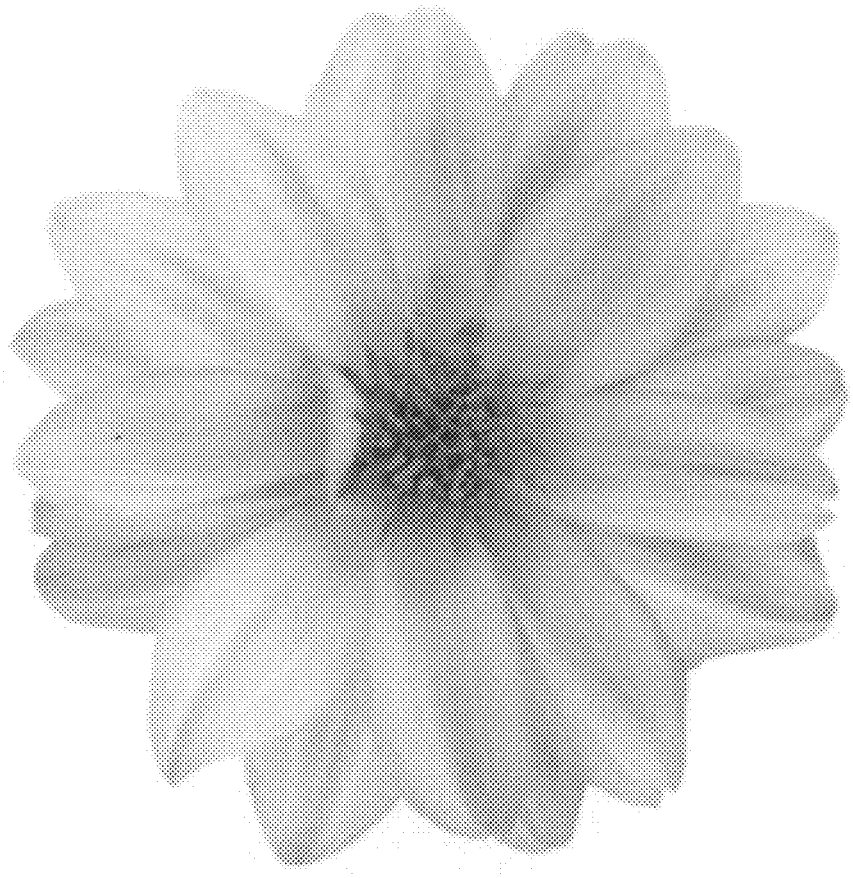

* * * * *